(12) United States Patent
Yatscoff et al.

(10) Patent No.: US 6,306,871 B1
(45) Date of Patent: Oct. 23, 2001

(54) ACTIVATED IODODERIVATIVES FOR THE TREATMENT OF CANCER AND AIDS

(76) Inventors: Randall W. Yatscoff, 215 Buchanan Close, Edmonton, Alberta (CA), T6R 2B7; Robert T. Foster, 4211 120th Street, Edmonton, Alberta (CA), T6J 1X9; Selvaraj Naicker, 3304-117th Street, Edmonton, Alberta (CA), T6J 3J4

( * ) Notice: Subject to any disclaimer, the term of this patent is extended or adjusted under 35 U.S.C. 154(b) by 0 days.

(21) Appl. No.: 09/665,654

(22) Filed: Sep. 19, 2000

Related U.S. Application Data

(63) Continuation of application No. 09/125,173, filed as application No. PCT/IB98/00768 on Aug. 11, 1998, now Pat. No. 6,225,323.
(60) Provisional application No. 60/043,360, filed on Apr. 10, 1998.

(51) Int. Cl.$^7$ ...................... A61K 31/437; A61K 31/426; A61K 31/4406; C07D 213/56; C07D 277/44; A61P 35/00
(52) U.S. Cl. .................. 514/292; 514/354; 514/355; 514/363; 514/365; 514/370; 514/457; 514/475; 514/563; 514/619; 514/371; 546/84; 546/298; 546/316; 546/324; 548/139; 548/190; 548/195; 548/201; 548/204; 548/136; 549/399; 549/550; 562/434; 564/166; 564/164
(58) Field of Search ..................... 546/316, 324, 546/84; 548/190, 201, 204, 136; 549/399, 550; 562/434; 564/166; 514/354, 355, 292, 363, 365, 370, 457, 475, 563, 619

(56) References Cited

U.S. PATENT DOCUMENTS 5,516,941   5/1996   Kun et al. .......................... 564/166
5,670,518   9/1997   Kun et al. .......................... 514/309

OTHER PUBLICATIONS

Berg, J. M., J. Biol. Chem., 265: 6513–6516, 1990.
Berg, J. M., Progress in Inorganic Chemistry, 37: 143–185, 1989.
Bravo, R., Cell Growth and Differentiation, 1: 305–309, 1990.
Evans, R. M., and Hollenberg, S. M., Cell, 52: 1–3, 1988.
Ueda et al., Annual Review of Biochemistry, 54, 73–100, 1985.
Boulikas, T., Toxicology Letters, 67, 129–150, 1993.
de Murcia et al., Trends in Biochemical Sciences, 19, 172–175, 1994.
Shall, S., Advances in Radiation Biology, 11, 1–69, 1984.
Clever, J.E. et al., Mutation Research, 257, 1–18, 1991.
Lautier et al., Molecular and Cellular Biochemistry, 122, 171–193, 1993.
Kaufmann et al., Cancer Research, 53, 3976–3985, 1993.
Mendeleyev, J. et al., Biochemical Pharmacology, 50, 705–714, 1995.
Rice et al., Science, 270, 1194–1197, 1995.

*Primary Examiner*—Evelyn Mei Huang
(74) *Attorney, Agent, or Firm*—Burns, Doane, Swecker & Mathis LLP

(57) ABSTRACT

A series of activated iodo-benzamide derivatives are described as antineoplastic and antiviral drug compounds. The compounds generally possess a chelating group, a thiol trapping group and an activating group. The presumptive mechanism of action in preventing cancer cell and virus replication is through inhibition of the binding of transcription factors to zinc finger binding domains. The compounds are effective in inhibiting growth of a variety of human and animal tumor and leukemia cell lines at low concentrations.

4 Claims, No Drawings

ACTIVATED IODODERIVATIVES FOR THE TREATMENT OF CANCER AND AIDS

This application is a continuation of application Ser. No. 09/125,173, filed Aug. 11, 1998 U.S. Pat. No. 6,225,323.

REFERENCE TO RELATED APPLICATIONS

This application was filed as PCT/IB98/00768 on Apr. 10, 1998 which is a continuation-in-part of U.S. provisional application No. 60/043,360, which are relied upon and incorporated by reference.

INTRODUCTION AND BACKGROUND

This invention is related to synthesis of activated iodo derivatives and their use as antineoplastic and antiviral agents by targeting the zinc finger regions of metalloregulatory proteins such as p-ADPRT and nucleocapsid of HIV. A series of activated iodo-benzamide derivatives are described as antineoplastic and antiviral drug compounds. The compounds generally possess a chelating group, a thiol trapping group and an activating group. The presumptive mechanism of action in preventing cancer cell and virus replication is through inhibition of the binding of transcription factors to zinc finger binding domains. The compounds are effective in inhibiting growth of a variety of human and animal tumor and leukemia cell lines at low doses.

Zinc Finger Proteins

In the past several years, a series of discoveries revealed that several proteins contain metal ions, particularly zinc ions ($Zn^{2+}$), that play fundamental roles in stabilizing specific protein conformations (Berg, J. M., J. Bioj. Chem., 265: 6513–6516, 1990; Berg, J. M., In Progress in Inorganic chemistry, 37: 143–190, 1989). Many of these metalloproteins are involved in nucleic acid binding and in gene regulation (Bravo, R., Cell Growth and Differentiation, 1: 305–309, 1990; Evans; R. M., and Hollenberg, S. M., Cell, 52: 1–3, 198).

The nuclear eukaryotic enzyme poly(ADP-ribose) polymerase [PARP (EC 2.4.2.30)] catalyzes the transfer of the ADP-ribose moiety of nictotinamide adenine dinucleotide (NAD+) to nuclear aceptor proteins, in response to DNA strand-break formation (Udea et al., Annual Review of Biochemistry, 54, 73, 1985; Boulikas, T., Toxicology Letters, 67, 129, 1993; De Murcia et al., Trends in Biochemical Sciences, 172, 1994). The protein-bound linear and branched-chain homo-ADP polymers thus formed are implicated in a number of important cellular processes, including:

1. DNA repair—Shell, S., Advances in Radiation Biology, 11, 1, 1984; Clear, J. E. et al., Mutation Research, 257, 1, 1991.
2. Cellular differentiation—Lautier et al., Molecular and Cellular Biochemistry, 122, 171, 1993.
3. Gene expression—Boulikas, T., Toxicology Letters, 67, 129, 1993.
4. Apoptosis—Kaufmann et al., Cancer Research, 53, 3976, 1993.

The human enzyme (116 kDa) is multifunctional and comprises an N-terminal DNA binding (46 kDa) containing two zinc fingers, a central automodification site (22 kDa) and a C-terminal domain (54 kDa).

Apoptosis and ADPRT

Apoptosis, or programmed cell death, plays an essential role in specific cell deletion during normal embryonal and adult development. Apoptotic cells are characterized by fragmentation of nuclear DNA and formation of apoptotic bodies. Molecular genetic analysis has revealed the involvement of several deaths and survival genes that are regulated by extracellular and intracellular factors. There are multiple inducers and inhibitors which interact with target cell specific receptors and transduce signals involved in cellular proliferation, cell cycle progression and programmed cell death. The elimination of tumor cell populations by applying lethal doses of chemotherapeutic agents or radiation is a well-established strategy in cancer therapy. Recent discoveries in the field of apoptotic cell death promise to have a significant impact on antitumor therapies. Apoptosis is known to be an active process which can be artificially manipulated by several molecular pathways.

Poly ADPRT has been consistently linked to the DNA repair process. ADP ribosylation levels have been mechanistically associated to human disease after activation of poly ADPRT by DNA damage by external sources. Firstly, poly ADPRT activity is dose-dependently up-regulated by reduced glutathione and down regulated by oxidized glutathione which establishes redox regulation of the enzyme. Secondly, the two zinc fingers in the two DNA binding domain of the poly ADPRT gene cysteine residues which, if oxidized, would presumably prevent DNA binding and participation in DNA repair.

The use of aromatic C-nitroso derivatives has been described in U.S. Pat. No. 5,516,941 for the treatment of diseases caused by viruses. The chemotherapeutic activity of an iodonitro derivative has been reported by Mendeleyev (Biochemical Pharmacology, 50, 705–714, 1995). The importance of the formation of a nitroso group for the compound's activity was disclosed in U.S. Pat. No. 5,670,518. The disclosed data were obtained with reduced glutathione thus indicating that the existence of free sulfide ion seems to be important for the activity of the reported compounds. Zinc fingers involve sulfide ions in the co-ordination of the metal ion, namely $Zn^{2+}$. In the disclosed zinc ejection experiments, EDTA was used as one of the reagents and no data were provided in the absence of EDTA. Disulfide substituted benzamide has been shown as a zinc finger inhibitor (Turfin et al., Science, 270, 1194, 1995).

The compounds described by this invention have combined and enhanced functionalties which inhibit cancer cell and virus replication by binding to and disrupting zinc finger binding domains. They exhibit high efficacy in inhibiting cancer cell growth in vitro.

SUMMARY OF THE INVENTION

In one aspect, the present invention relates to compounds for use in the treatment of neoplastic and viral diseases having the formula:

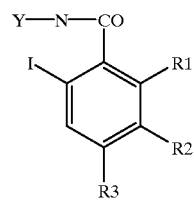

wherein Y is a chelating groups selected from the group of aliphatic, aromatic, heterocyclic, carbohydrate groups, and where Y and N together form a heterocyclic ring, R2 and R3 are the same or different and are H, NO2 or NH2, and R1 is NO2 or NH2 and when R2 is NH2 then R1 and R2 are H.

In a more detailed aspect, the invention relates to compounds of the formula:

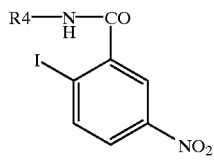

wherein R4 is H, —CH2CH=CH2, —CH2C≡CH, —NHC≡CH, —NHCH=CH2, OH,

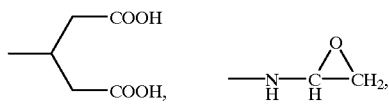

—(CH2)a N(R5)(R6) wherein a=1 or 2 and R5 and R6 are H, or lower alkyl,

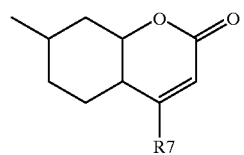

wherein R7 is H or CF3,

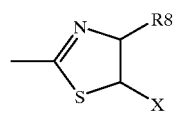

wherein X is H, NO2, —COOCH2, CH2, or CH3 and R8 is H or CH3,

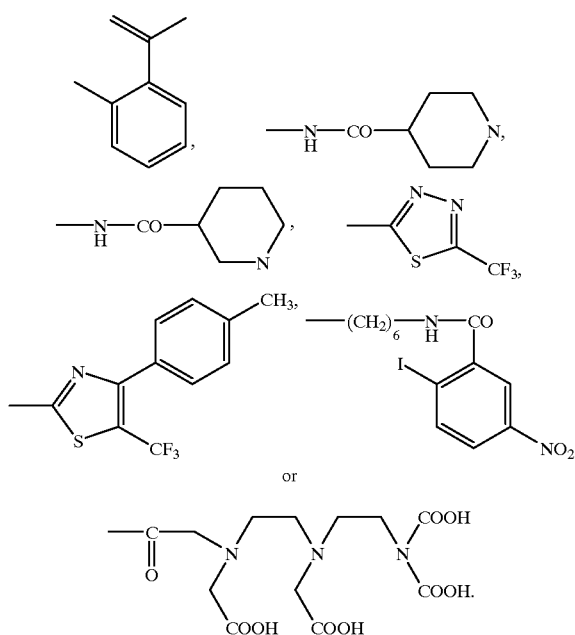

In another aspect, the invention relates to compounds of the formula:

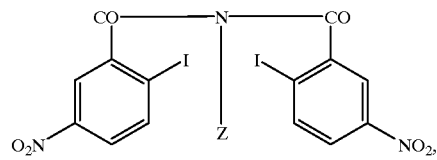

wherein Z is

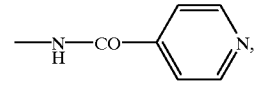

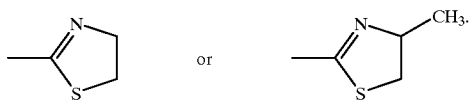

A still further aspect are the compounds:

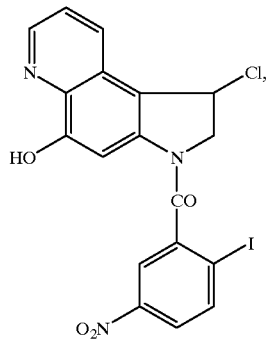

and

An additional aspect of the invention are pharmaceutical compositions comprising the above compounds with a pharmaceutically acceptable excipient and the pharmaceutical compositions for use in the treatment of neoplastic or viral diseases.

DETAILED DESCRIPTION OF THE INVENTION

A series of activated iodo derivatives has been developed to target zinc fingers based upon the following considerations:

1. A group acting as a competing chelating agent or sequestration agent.

2. A functional group or groups to trap the released sulfide moiety.
3. A functional group or groups to activate the functional trapping group.
4. Conformation of the molecule to facilitate receptor/ligand interaction

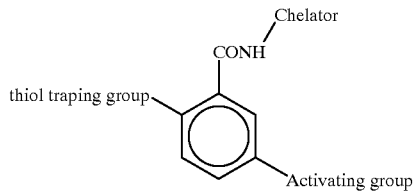

Not being bound by any theory, the proposed mechanisms of action of these compounds are as follows:
1. The chelating group at the amide linkage sequesters the zinc ion from the zinc fingers.
2. As soon as the Zn ion is depleted from the system, the free thiol group generated will react with the functional group at the ortho position of the molecule forming a stable non-reversible linkage. The iodo group is selected for this purpose. The nucleophilic sulfide ion displaces the iodo group.
3. The displacement of the iodo group is facilitated by the activating group, namely an electron withdrawing group. For our purpose we have selected one or two nitro or groups.

By the above mechanism, the molecules described in this invention, can react with thiols at the zinc finger DNA binding domain of poly ADP-ribosyl transferase to inhibit DNA repair and thereby increase DNA damage leading to apoptosis.

The synthesis of the derivatives involve the steps of: (1) synthesis of 2-iodo-5-nitrobenzoic acid, and (2) attachment of the chelator to the basic structure at the proper position.

PART I

2-Iodobenzoic acid is nitrated by conventional synthetic procedures. The crude 2-Iodonitrobenzoic acid is purified by conversion to methyl 2-iodo-5-nitrobenzoate in the pure form. This compound crystallizes out from the reaction mixture. The ester is hydrolyzed back to the acid with high purity. Alternatively, the acid can be purified by extracting in bicarbonate solution, neturalizing, filtering, and crystallized from ethyl alcohol.

PART II

Method A:

The 2-iodo-5-nitrobenzoic acid is treated with thionyl chloride to obtain the respective acid chloride. Without further purification, the acid chloride is reacted with the chelator through the amino group. For the preparation of the amide derivative, the methyl ester is treated with large excess of anhydrous ammonia over a period of 5 days at room temperature.

Method B:

The acid derivative is dissolved in dry DMF and treated with a carbodiimide derivative to form the active ester which is subsequently treated with the chelating group having an amino group. The resultant reaction mixture is stirred for 24 hours and filtered. The reaction mixture is concentrated and poured into water. The solid separated was filtered, washed with bicarbonate solution and purified by crystallization or column chromatography.

A summary of the synthetic procedure is presented in scheme 1 together with several non-limiting examples of chelating groups. Using this approach the derivatives shown in Table 1 were prepared.

TABLE 1

| Ref. No. | Structure | Molecular Weight | Melting Point |
|---|---|---|---|
| 1 | CONH(CH$_2$)$_2$NMe$_2$, I, NO$_2$ (benzene ring) | 363 | 126–128° C. |
| 2 | CONH(CH$_2$)$_2$NEt$_2$, I, NO$_2$ (benzene ring) | 391 | 124–126° C. |
| 3 | NO$_2$, CONH, I (benzene ring) linked to coumarin with CF$_3$ | 504 | 223–227° C. |

TABLE 1-continued

| Ref. No. | Structure | Molecular Weight | Melting Point |
|---|---|---|---|
| 4 | 2-iodo-5-nitro-N-(2-oxo-2H-chromen-7-yl)benzamide | 436 | 273–277° C. |
| 5 | 2-iodo-5-nitro-N-(thiazol-2-yl)benzamide | 375 | 210–213° C. |
| 6 | 2-iodo-5-nitro-N-(5-nitrothiazol-2-yl)benzamide | 420 | 230–234° C. |
| 7 | N-allyl-2-iodo-5-nitrobenzamide (CONHCH$_2$CH=CH$_2$) | 332 | 155–158° C. |
| 8 | 2-iodo-5-nitro-N-(prop-2-yn-1-yl)benzamide (CONHCH$_2$C≡CH) | 330 | 204–206° C. |
| 9 | 2-iodo-5-nitro-N-(2-(prop-1-en-2-yl)phenyl)benzamide | 498 | 155–158° C. |
| 10 | N'-(2-iodo-5-nitrobenzoyl)isonicotinohydrazide (CONHNHCO-pyridyl) | 412 | 256–259° C. |

TABLE 1-continued

| Ref. No. | Structure | Molecular Weight | Melting Point |
|---|---|---|---|
| 11 | 4-nitro-2-iodo-benzoyl-NHNHCO-pyridin-3-yl | 412 | 217–221° C. |
| 12 | bis(4-nitro-2-iodo-benzoyl)N-NHCO-pyridin-3-yl | 687 | |
| 13 | 5-amino-2-iodo-benzamide | 278 | 255–258° C. |
| 15 | 5-nitro-2-iodo-benzamide | 292 | 260–264° C. |
| 16 | 5-nitro-2-iodo-benzoyl-NH-(4-methyl-5-ethoxycarbonyl-thiazol-2-yl) | 461 | 211–212° C. |
| 17 | bis(5-nitro-2-iodo-benzoyl)N-(4,5-dihydro-thiazol-2-yl) | 652 | |
| 18 | 5-nitro-2-iodo-benzoyl-N-(5-trifluoromethyl-1,3,4-thiadiazol-2-yl) | 444.13 | 219–221° C. |

TABLE 1-continued

| Ref. No. | Structure | Molecular Weight | Melting Point |
|---|---|---|---|
| 19 | 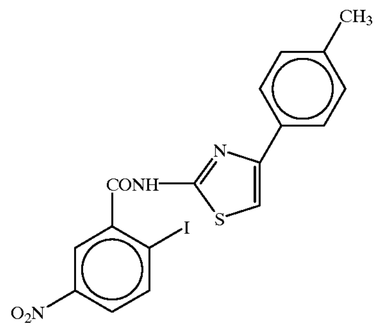 | 465 | 244–248° C. |
| 20 | 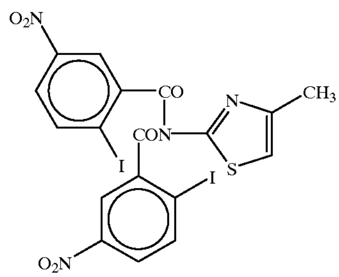 | 664 | |
| 21 | 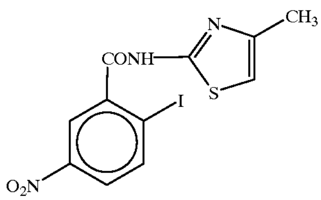 | 389 | 180–181° C. |
| 22 | 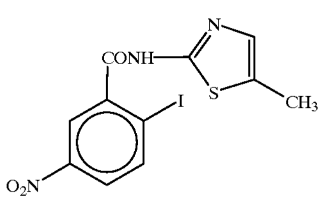 | 389 | 218–224° C. |
| 23 | 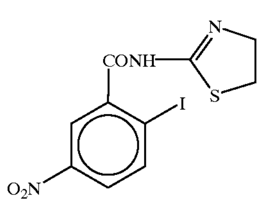 | 377 | 176–179° C. |
| 24 | 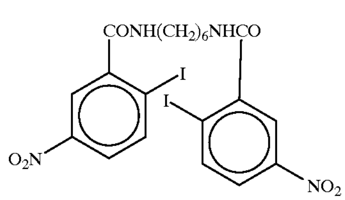 | 666.20 | |

EXAMPLE 1

2-Iodo-5-Nitrobenzoic Acid

2-Iodobenzoic acid (100 g) was dissolved in 400 mL of concentrated sulphuric acid and placed in a 2 liter 3 necked flask. The flask was fitted with reflux condenser, a thermometer and an addition funnel. Fuming nitric acid (400 ml) was added drop by drop. The addition was adjusted in such a way that the temperature was allowed to raise to 80° C. over a period of 2 hours. During the addition, the reaction mixture was stirred vigorously and maintained the temperature at 80° C. for an additional 2 hours. After the completion of the reaction, the reaction mixture was poured slowly into crushed ice (3 Kg). The contents were allowed to settle and were filtered. The yellow precipitate was collected and dried at 30° C. The yield was 90 grams.

EXAMPLE 2

Methyl 2-Iodo-5-Nitro-Benzoate

In a 5 liter 3 necked flask, 2-iodo-5-nitro-benzoic acid (100 grams) was dissolved in methanol (3000 ml). The flask was fitted with a reflux condenser and 50 ml of concentrated sulfuric acid was added carefully with cooling. After the completion of the addition, the contents were refluxed for 3 days until completion of the reaction. The reaction was followed by TLC. After the completion of the reaction, the reaction mixture was concentrated to 1000 ml and allowed to cool. The product crystalized as a light yellow colored powder. The solid material was filtered and washed with water and methanol and air-dried. The yield was 90 grams.

EXAMPLE 3

2-Iodo-5-Nitro-Benzamide: (15)

In a 10 liter 3-necked flask, purified methyl-2-iodo-5-nitro-benzoate (100 grams) was dissolved in anhydrous methanol (4000 ml). The reaction flask was fitted with a mechanical stirrer. The solution was saturated with anhydrous ammonia gas for three hours, with ice cooling. The reaction mixture was stirred for 5 days. Fresh ammonia gas was bubbled through the solution in the interval of 12 hours. The reaction was followed by TLC and was completed after 5 days. Nitrogen gas was bubbled through the reaction solution to remove the excess of dissolved ammonia gas. The reaction solution was then concentrated to 1500 ml and the product allowed to crystallize overnight. The solid material was filtered washed with ice-cold methanol and air dried. The solid was recrystalized from ethanol. The yield was 80 grams.

EXAMPLE 4

(N ,N-Dimethylamincethyl)-2-Iodo-5-Nitro-Benzamide (1)

2-iodo-5-nitro-benzoic acid (3 mmoles) was dissolved in a solution of dry dichloromethane-DMF mixture (v/v 4:1, 5 ml). To the ice-cold solution, was added 6 mmoles of thionyl chloride. The reaction mixture was stirred at room temperature for two hours. The solvent was then evaporated using a rotory evaporator. The residue was dried under vacuum at 50° C. for 30 minutes. The residue was dissolved in dry dichlormethane (5 ml) without any purification. The solution was then cooled to 0° C. To this solution, triethylamine (1 ml) and a solution of N,N-dimethylethylenediamine (3 mmole) in dichloromethane was added. The reaction mixture was stirred at room temperature for 16 hours. After completion of the reaction, the reaction mixture was poured into water and basified to pH 12 using 2M NaOH. The organic layer was separated and washed with water, dried over anhydrous magnesium sulfate and concentrated. The (N,N-dimethylaminoethyl)-2-iodo-5-nitro-benzamide compound was separated by silica gel chromatography. The yield was 70%. The melting point was 126–128° C.

$^1$H NMR (CDCl3) δ 2.27(s 6H, CH3); 2.55(t J=5.7 Hz, 2H, CH2N—); 3.55(q, J=5.7 Hz, 2H, CONHCH2—); 6.56 (br s, 1H, NH); 7.93(dd, J=3.0 Hz, j=8.7 Hz, 1H, phenyl, H=4); 8.21(d, J=3.0 Hz, 1H, phenyl H=6)

EXAMPLE 5

(N,N -Diethylaminoethyl)-2-Iodo-5-Nitro-Benzamide (2)

Prepared as per the method described in example 4 with a yield of 75%.

$^1$H NMR (CDCl3) δ 1.04(t, J=7.2 Hz, 6 h, CH2CH2); 2.58(q, J=7.2 Hz, 4H, CH3CH2—), 2.69(t, J=5.7 Hz, 2H, CH2N—)2); 3.53(q, J=5.7 Hz, 2H, CONHCH2—); 6.64(br., s, 1H, NH); 7.93(dd J=3.0 Hz, J=8.7 Hz, 1H, Aromatic H-3); 8.10 (d, J=8.7 Hz, 1H, Aromatic H-4); 8.21(d, J=3.0 Hz, Aromatic H-6). The melting point was 124–125° C.

EXAMPLE 6

N-(Allyl)-2-Iodo-5-Nitro-Benzamide (7)

Prepared as per the method described in example 4. The yield was 58%. The melting point was 155–158° C.

$^1$H NMR(CDCl3) (δ 8.80(t, J=5.4 Hz, 1H, NH); 8.20(d, J=8.4 Hz, 1H, phenyl H-4); 8.07(d, J=2.7 Hz, 1H, phenyl H-6); 7.96 (dd, J=8.4 Hz, J=2.7 Hz, 1H, phenyl H-3); 5.85–5.98(m, 1H, CH=); 5.30 (dd, J=17.7 Hz, J=1.5 Hz, 1H, =CH); 5.14(dd, J=10.5 Hz, J=1.5 Hz, 1H, =CH); 3.88–3.11(m, 2H, CH2—)

EXAMPLE 7

N-(Propargyl) 2-Iodo-5-Nitro-Benzamide (8)

Prepared as per the method described in example 4. The yield was 20%. The melting point was 204–206° C.

$^1$H NMR(CDCl3) δ 9.10(t, J=5.1 Hz, 1H, NH); 8.20(d, J=8.4 Hz, 1H, phenyl H-6); 7.97(dd, J=8.4 Hz, J=2.7 Hz, 1H, phenyl H-3); 8.04(d, J=2.7 Hz, 1H, phenyl H-6) 4.07 (dd, J=2.4 Hz, J=5.4 Hz, 2H, —CH2—); 3.21 t, J=2.4 Hz, acetylenic H)

EXAMPLE 8

N-(2'-Iodo-5'-Nitro-Benzoyl) 2-Isopropenyl Aniline (9)

Prepared as per the method described in example 4. The melting point was 155–158 C.

$^1$H NMR: (CDCl3) δ: 8.42 (d, J=8.1 Hz, 1H, phenyl H-6'), 8.29 (d, J=2.4 Hz, 1H, phenyl H-2'); 8.15 (d, J=9.0 Hz, phenyl H-6); 7.989 (dd, J=8.1 Hz, J=2.4 Hz, 1H, phenyl H-5), 7.91 (s, 1H, NH); 7.34–7.40 (m, 1H, phenyl H-3'); 7.17–7.25 (m, 2H, phenyl H-4 & H-50; 5.39 (d, J=1.2 Hz, 1H, vinyl H); 5.10 (d, J=1.2 Hz, 1H, vinyl-H), 2.12 (s, 3H, CH3)

EXAMPLE 9

7-(2'-Iodo-5'-Nitro-Benzamido)-4-Trifluoromethyl-2H-1-Benzopyran-2-one (3)

Prepared as per the method described in example 4. The yield was 10%. The melting point was 223–227° C.

$^1$H NMR: (DMSO-d6) δ 11.22 (s, 1H, NH); 8,39 (d, J=2.4 Hz, phenyl H-6'); 8.29 (d, J=8.7 Hz, 1H, phenylH-4'); 8.06 (dd, J=8.7 Hz, J=2.4 Hz, 1H, phenyl H-3'); 7.96 (d, J=1.5 Hz, 1H, benzopyran H-8); 7.77 (dd, J=9 Hz, J=1.5 Hz, 1H, benzopyran H-6); 7.68 (dd, J=9 Hz, J=1.5 Hz, 1H, benzopyran H-3)

EXAMPLE 10

7-(2'-Iodo-5'-Nitro-Benzamido)-2H-1-Benzopyran-2-one (4)

Prepared as per the method described in example 4. The yield was 15%. the melting point was 273–277° C.

$^1$H NMR: (DMSO-d$_6$) δ 10.86(s, 1H, NH); 8.33 (d, J=2.7 Hz, 1H, phenyl H-6'); 8.27(d, J=8.7 Hz, 1H, phenyl H-4'); 8.20 (d, J=2.4 Hz, Benzopyran H-6); 8.17(d, J=9.9 Hz, 1H, benzopyran H-4'); 8.04(dd, J=8.7 Hz, J=2.7 Hz, 1H, phenyl H-3'); 7.76 (dd, J=8.7 Hz, J=2.4 Hz, 1H, benzopyran H-7); 7.45 (d, J=8.7 Hz, 1H, benzopyran H-8); 6.53(d, J=9.9 Hz, 1H, benzopyran, H-3)

EXAMPLE 11

2-(2'-Iodo-5'-Nitro-Benzamido)-Thiazole (5)

Prepared as per the method described in example 4. The yield was 16%. The melting poing was 210–213° C.

$^1$H NMR: (DMSO-d$_6$) δ 12.85(b.s., 1H, NH); 8.38 (d, J=2.7 Hz, 1H, phenyl H-6'); 8.26 (d, J=8.4 Hz, 1H, phenyl H-4'); 8.04 (dd, J=8.4 Hz, J=2.7 Hz, 1H, phenyl H-3'); 7.57 (d, J=3.6 Hz, 1H, thiazole H-4); 7.36 (d, J=3.6 Hz, 1H, thiazole H-5)

EXAMPLE 12

2-(2'-Iodo-5'-Nitro-Benzamido)-5-Nitro-Thiazole (6)

Prepared as per the method described in example 4. The yield was 13%. The melting point was 230–234° C.

$^1$H NMR: (DMSO-d$_6$) δ 13.5–14.00 (br, 1H, NH 0; 8.72(s, 1H, nitrothioazole H-4);8.52 (d, J=2.7 Hz, 1H, phenyl H-6'); 8.30 (, J=8.7 Hz, 1H, phenyl H-4); 8.09 (dd, J=8.7 Hz, phenyl H-4'); 8.09 (dd, J=8.7 Hz, J=2.7 Hz, 1H, phenyl H-3')

EXAMPLE 13

N-(4'-Pyridyl)-2-Iodo-5-Nitrophenyl Hydrazide(10)

Prepared as per the method described in example 4. The yield was 55%. The melting point was 256–259° C.

$^1$H NMR: (DMSO d$_6$) δ 11.11 (s, 1H, NH); 10.79 (s, 1H, NH); 8.81 (d, J=5.7 Hz, 2H, pyridyl H-3, H-5); 8.29 (d, J=8.4 Hz, 1H, phenyl H-3); 8.18 (d, J=2.7 Hz, 1H, phenyl H-6); 8.06 (dd, J=8.4 Hz, J=2.7 Hz, 1H, phenyl H-4); 7.86 (d, J=5.7 Hz, 2H, pyridyl H-2, H-6)

EXAMPLE 14

N-(3'-Pyridyl)-2-Iodo-5-Nitrophenyl Hydrazide (11)

Prepared as per the method described in example 4. The melting point was 255–258° C.

$^1$H NMR: (DMSO d$_6$) δ 11.01 (s, 1H, NH); 10.76 (s, 1H, NH); 9.10 (d, J=1.5 Hz, 1H, pyridyl H-2); 8.79 (dd, J=4.8 Hz, J=1.5 Hz, 1H, pyridyl H-6); 8.28–8.31 (m, 1H, pyridyl H-4); 8.29 (d, J=8.7 Hz, 1H, phenyl H-3); 8.18 (d, J=2.7 Hz, 1H, phenyl H-6); 8.06 (dd, J=8.7 Hz, J=2.7 Hz, 1H, phenyl H-4); 7.59 (dd, J=7.8 Hz, J=4.8 Hz, 1H, pyridyl H-5)

EXAMPLE 15

2-(2'-Iodo-5'-Nitro-Benzamido)-3-Methyl-4-Ethylcarboxy-Thiazole (16)

The melting point was 211–212° C.

$^1$H NMR: (DMSO d$_6$) δ 13.25 (s, br, 1H, NH); 8.43 (d, J=2.7 Hz, 1H, phenyl H-6); 8.27 (d, J=8.7 Hz, 1H, phenyl H-3); 8.05 (dd, J=8.7 Hz, J=2.7 Hz, 1H, phenyl H-4); 4.27 (q, J=6.9 Hz, 2H, CH$_2$CH$_3$); 2.59 (s, 3H, CH$_3$); 1.31 (t, J=6.9 Hz, CH$_3$CH$_2$)

EXAMPLE 16

2-(2'-Iodo-5'-Nitro-Benzamido)-2-Thiazoline (17)

The melting point was 176–179° C.

$^1$H NMR: (DMSO d$_6$) δ 9.94 (s, br, 1H, NH); 8.52 (d, J=2.7 Hz, 1H, phenyl H-6); 8.31 (d, J=8.4 Hz, 1H, phenyl H-3); 8.01 (dd, J=8.4 Hz, J=2.7 Hz, 1H, phenyl H-4); 3.75 (t, J=7.5 Hz, 2H, thiazoline H-4); 3.38 (m. 2H, thiazoline H-5)

EXAMPLE 17

2-(2'-Iodo-5'-Nitro-Benzamido)-5-Trifluoromethyl-1,2,4-Thiadiazole (18)

The melting point was 219–221 ° C.

$^1$HNMR: (DMSO d$_6$) δ 14.02 (s, br, 1H, NH); 8.53 (d, J=2.7 Hz, 1H, phenyl H-6), 8.30 (d, J=8.7 Hz, 1H, phenyl H-3); 8.10 (dd, J=8.7 Hz, J=2.7 Hz, 1H, phenyl H-4)

EXAMPLE 18

2(2'-Iodo-5'-Nitro-Benzamido)-4-tolyl-Thiazole (19)

The melting point was 244–248° C.

$^1$H NMR: DMSO d$_6$) δ 12.98 (s, 1H, NH); 8.41 (d, J=2.7 Hz, 1H, phenyl H-6); 8.26 (d, J=8.4 Hz, 1H, phenyl H-3); 8.05 (dd, J=8.4 Hz, J=2.7 Hz, 1H, phenyl H-4); 7.81 (d, J=8.1 Hz, 2H, tolyl, H-3, H-5); 7.69 (s, 1H, thiazole H-5) 7.25 (d, J=8.1 Hz, 2H, tolyl H-2, H-6); 2.33 (s, 3H, CH$_3$)

EXAMPLE 19

2-(2'-Iodo-5'-Nitro-Benzamido)-4-Methyl-Thiazole (21)

The melting point was 218–224° C.

$^1$H NMR: (DMSO d$_6$) δ 12.78 (s, br, 1H, NH); 8.36 (d, J=2.7 Hz, 1H, phenyl H-6); 8.25 (d, J=8.7 Hz, 1H, phenyl H-3); 8.03 (dd, J=8.7 Hz, J=2.7 Hz, 1H, phenyl H-4); 6.89 (s, 1H, thiazole H-5); 2.29 (s, 3H, CH$_3$)

EXAMPLE 20

2(2'-Iodo-5'-Nitro-Benzamido)-5-Methyl-Thiazole (22)

The melting point was 180–181° C.

$^1$H NMR: (DMSO d$_6$) δ 12.78 (s, br, 1H, NH); 8.36 (d, J=2.7 Hz, 1H, phenyl H-6); 8.25 (d, J=8.7 Hz, 1H, phenyl H-3); 8.03 (dd, J=8.7 Hz, J=2.7 Hz, 1H, phenyl H-4); 6.89 H-5); 2.29 (s, 3H, CH$_3$)

EXAMPLE 21

1,6-Di-(2'-Iodo-5'-Nitro-Benzamido)-Hexane(24)

$^1$H NMR: (DMSO d$_6$) δ 8.59 (t, J=5.7 Hz, 2H, NH); 8.18 (d, J=8.4 Hz, 2H, phenyl H-3); 8.03, (d, J=2.7 Hz, 2H, phenyl H-6); 7.95 (dd, J=8.4 Hz, J=2.7 Hz, 2H, phenyl H-4); 3.22–3.29 (m, 4H, CH$_2$NH); 1.3–1.65 (two br m, 8H, (CH$_2$)$_4$)

In Vitro Activity
Materials and Methods

Cell culture: The human cell lines were propagated under sterile conditions in RPMI 1640 (CellGrow) with 10% fetal bovine serum (Hyclone), 2 mM L-glutamine, and sodium bicarbonate (complete medium) and incubated at 37° C. in HEPA-filtered Sterilcult $CO_2$ tissue culture incubators (Forma) with 5% $CO^2$ and 95% humidity (Table 1). The murine leukemia cell lines were propagated in Dulbecco's MEM media with 10% equine serum (Hyclone), 2 mM L-glutamine, and sodium bicarbonate (complete medium) and incubated as described. The cells were subcultured twice weekly and used in experiments. The culture was screened for mycoplasma contamination using GeneProbetm (Fisher) and positive cultures were cured of contaminants over three passages using constant treatment with BM-Cyclin™ antibiotic combination (Boehringer Mannheim). Only cultures confirmed as mycoplasma free were used in testing compounds for anticellular activity.

TABLE 2

| CELL LINE | ORIGIN |
| --- | --- |
| COLO 205 | Colon Adenocarcinoma |
| A549 | Bronchogenic |
| RPMI 8226 | Myeloma |
| MCF7 | Breast Adenocarcinoma |
| M14 | Melanoma |
| SK-MEL-5 | Melanoma |
| SK-PV-3 | Ovarian Adenocarconoma |
| B16 | Murine Melanoma |
| L1210 | Murine Leukemia |
| P388 | Murine Leukemia |

Test Samples

The test compounds were stored at 4° C. under light protected conditions. The test compounds were weighed and dissolved in DMSO. The dissolved compounds were then serially diluted in warm medium (RPMI 1640 or Dulbecco's MEM) under constant mixing to minimize precipitation. The positive control drug doxorubicin was diluted in water followed by dilution in media to achieve a final concentration of 200 nM.

Experimental Design

For all experiments, the cells were harvested and centrifuged to remove the media, and suspended in fresh completed medium. Samples were taken to determine cell density. The cell count was determined with a Coulter Model $Z_1$ cell counter and viability was measured with propidium iodide staining followed by analysis on a Coulter EPPICS Elite Flow cytometer. The cell samples sere adjusted with complete medium to a density of $5\times10^4$/mL for adherent cell lines and $1\times10^5$/mL for suspension lines. Tissue culture cluster plates (96 well, cat No. 3595 Costar for adherent human lines and cat No. 25850 Corning for murine leukemias) were seeded with 100 µL cells and incubated as described. Replicate groups of plates were set up for each line to accommodate the exposure options for single agents and combinations. For each dilution 8 wells (100 µL samples of cells) were treated with 100 µL of dosing solution one day after plating. Each cluster plate contained a cell control (8 wells, mock-treated with complete medium), a medium control (3 wells with medium used to subtract out signal generated by media conditions), and an air blank (1 well, for calibrating the plate reader).

Neutral Red Assay

Anticellular effects of the compounds for the adherent cell lines were assessed with neutral red dye. On the day of analysis, the media was removed from sample cell monolayers and replaced with 0.1 mL of neutral red solution (0.5% neutral red, HBSS:RPMI 1640 (1:1), 0.05 M HEPES, pH 7.2). After incubation of the samples at 37° C. for 1 hour the excess dye was removed with blotting and the monolayers were washed twice with 0.85% NaC1 solution (0.1 mL per wash). The cell associated dye was extracted by adding 0.2 mL of a 0.1 M $NaH_2PO_4$: ethanol (1:1) solution/well followed by incubation for 1 hour at 35° C. The absorbency of neutral red in each monolayer was measured at 550 nm (620 nm reference beam) on a Denley Anthos 2001 microplate reader. The data were transferred via the ARCOM software capture program in Lotus 1-2-3 for processing.

Crystal Violet Assay

In assays where technical difficulties due to crystalization of the neutral red occurred the crystal violet staining procedure was employed to measure the amount of cells were left on the plate. Crystal violet staining solution [0.5% crystal violet (w/v), 50% methanol (v/v), 45% saline (v/v), and 5% formalin (v/v)] were prepared on the day of staining. After the media was removed from the sample wells, two drops of crystal violet stain were added to each well and the samples were incubated at ambient temperature for 10 minutes. The excess stain was removed with decanting and flushing with water and the plates were allowed to dry overnight at ambient temperature. The absorbance was measured at 550 nm on a Denley Anthos 2001 microplate reader. The data were transferred via the ARCOM software capture program into Lotus 1-2-3 for processing.

XTT Assay

Anticellular effects of the murine leukemia cell lines were assessed with the XTT dye conversion assay which is more suited to suspension cultures. On the day of analysis XTT [2,3-bis (2-methoxy-4-nitro-5-sulfophenyl)-5-[phenylamino)carbenyl]-2H-tetrazolium hydroxide, inner salt, sodium salt (Sigma)] was weighed out and dissolved at 1 mg/mL in media. PMS (phenazine methosulfate) was prepared at 5 mM in PBS (phosphate buffered saline) and stored as a stock solution at 4° C. The PMS was mixed with dissolved XTT to a final concentration of 0.025 mM. Sample wells were treated with 50 µL of the XTT solution and the plates were incubated for four hours at 37° C. to allow for conversion into the liquid soluble formazan product. After the incubation period the reaction was stopped by adding 10 µL of 10% SDS solution per well and the wells contents of each plate were mixed by agitation. The absorbancy of formazan in each monolayer was measured at 450 nm (620 nm reference beam) on a Denley Anthos 2001 microplate reader. The data were transferred via the ARCOM software capture program into Lotus 1-2-3 for processing.

EXAMPLE 22

IC50 Assays:

Using the procedures described above, concentrations of the Example compounds necessary to inhibit cell proliferation and growth by 50% ($IC_{50}$ values) were determined in the test cells lines. The results are presented in Table 3.

TABLE 3

IC$_{50}$ Concentrations ($\mu$M) for the Example Compounds in Human and Animal Cell Lines

| Cell Line: Reference # | A 549 | B16 | M14 | MCF 7 | SK MEL-5 | SK-OV-3 | COLO 205 | RPM 18226 | L1210 | P388 |
|---|---|---|---|---|---|---|---|---|---|---|
| 1 | 332.86 | 47.9 | 473.87 | 133.42 | 40.11 | 404.11 | 266.78 | | 283.29 | 352.95 |
| 2 | 333.38 | 9.21 | | 128.15 | | 400.46 | 342.93 | | 122.82 | 379.71 |
| 3 | 362.55 | 15.84 | 126.08 | 114.05 | 37.74 | 44.01 | 39.88 | | 44.15 | 14.31 |
| 4 | >500.00 | 15.86 | >500.00 | >500.00 | >500.00 | 395.45 | >500.00 | | | |
| 5 | 48.55 | 30.79 | 17.42 | 26.98 | 46.23 | 132.79 | 13.4 | | | |
| 6 | 86.51 | 54.99 | 140.89 | 80.9 | 131.83 | 129.73 | 116.85 | | >6.17 | |
| 7 | 133.73 | 45.09 | 41.78 | | 124.01 | 46.37 | 38.49 | | | 39.42 |
| 8 | 46.56 | 50.04 | 49.03 | 47.67 | 90.42 | 43.42 | 30.58 | | | 25.8 |
| 9 | >500.00 | 462.07 | >500.00 | 100.19 | >500.00 | >500.00 | | | | |
| 10 | >500.00 | 300.87 | >500.00 | >500.00 | >500.00 | 360.8 | 441.08 | | >18.52 | >18.52 |
| 11 | 387.43 | 128.84 | 466.55 | | 413.09 | 381.33 | 110.97 | | 55.56 | >55.56 |
| 12 | 297.89 | 45.98 | 133.6 | 117.71 | 45.36 | 45.65 | 35.83 | | 39.82 | 39.73 |
| 13 | >500.00 | 499.87 | >500.00 | >500.00 | >500.00 | >500.00 | >500.00 | | | 439.03 |
| 14 | 346.85 | 35.74 | | 412.96 | 212.58 | 99.46 | 82.84 | | 131.93 | 117.52 |
| 15 | 37.35 | 133.87 | 36.14 | | 313.73 | 141.18 | 33.18 | | | |
| 16 | 30.12 | 7.93 | 37.29 | 34.32 | 41.73 | 41.19 | 31.23 | 10.58 | 41.11 | 11.22 |
| 17 | 126.62 | 27.89 | 37.89 | 46.88 | 42.79 | 32 | >500.00 | >500.00 | 29.19 | 0.9 |
| 18 | 15.67 | 20.78 | 27.29 | 24.04 | 28.82 | 73.01 | 41.29 | 15.71 | 28.38 | 12.84 |
| 19 | 162.56 | 5.15 | 14.43 | 35.5 | 51.34 | 33.18 | 18.23 | 11.75 | 13.54 | 2.43 |
| 20 | 48.38 | 8.46 | 15.1 | 36.1 | 47.08 | 10.84 | 42.63 | 13.67 | 38.45 | 11.72 |
| 21 | 43.66 | 5.13 | 13.16 | 12.5 | 15.04 | 15.7 | 5.59 | 3.33 | 12.84 | 3.44 |
| 22 | 45.2 | 5.2 | 14.51 | 14.81 | 15.3 | 16.09 | 13.5 | 12.66 | 12.83 | 3.64 |
| 23 | >500.00 | 128.6 | 150.5 | 161.6 | 124.7 | >500.00 | 81.89 | 236.8 | >500.00 | 352.9 |
| 24 | >500.00 | >500.00 | >500.00 | >500.00 | >500.00 | >500.00 | >500.00 | >500.00 | >500.00 | >500.00 |

As can be seen from the data in Table 3, the Example compounds show good to excellent efficacy in inhibiting growth of a variety of human and animal cancer cell lines.

Determination of the physicochemical, toxicological and pharmacokinetic properties can be made using standard chemical and biological assays and through the use of mathematical modeling techniques which are known in the chemical and pharmacological/toxicological arts. The therapeutic utility and dosing regimen can be extrapolated from the results of such techniques and through the use of appropriate pharmacokinetic and/or pharmacodynamic models.

The compounds of this invention may be administered neat or with a pharmaceutical excipient/carrier to an animal in need thereof including human patients. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, possibly sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The pharmaceutical composition can be in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the physician.

As will be seen from the foregoing Examples, procedures not described in detail are conventional. Variations and modifications will be apparent to those skilled in the art and are intended to be encompassed by the above descriptions and the claims appended hereto.

Scheme 1
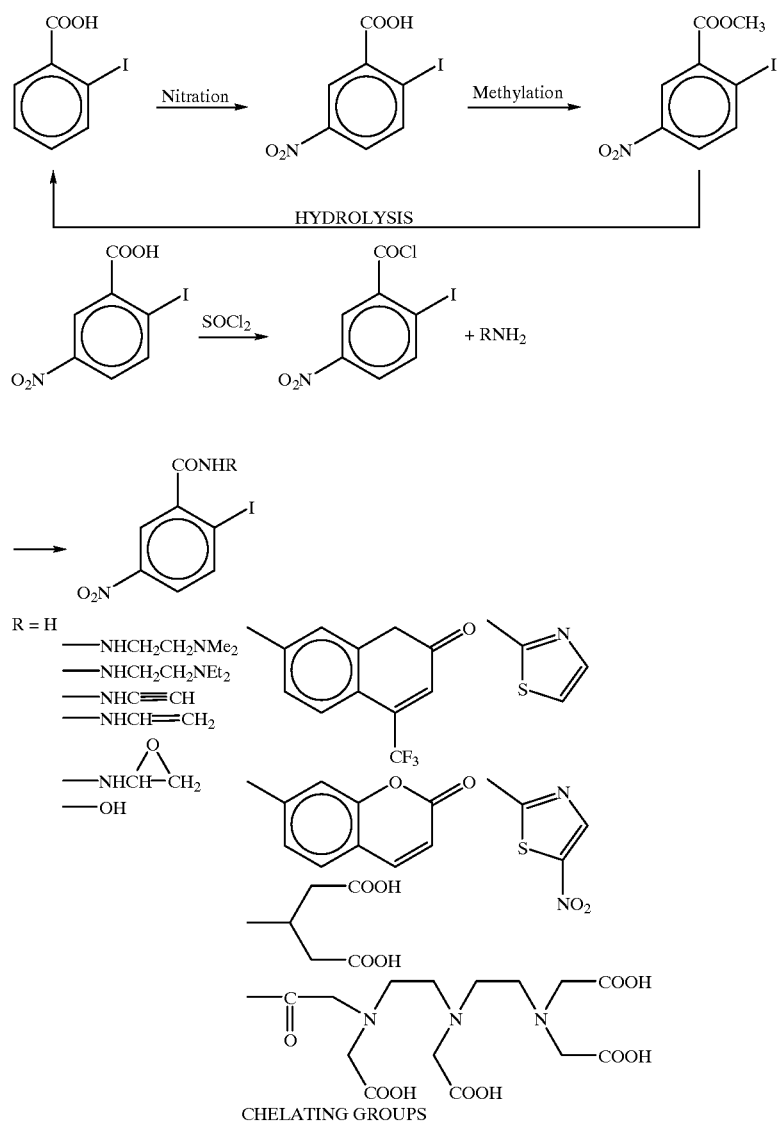
What is claimed is:
1. A compound represented by the formula:
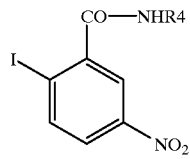
wherein:
R4 is:
(i) —CH$_2$CH=CH$_2$,
(ii) —CH$_2$CH=CH,
(iii) —NHCH=CH$_2$,
(iv) —NHCH=CH,
(v) OH,
(vi)
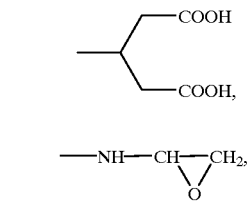
(viii) —(CH$_2$)$_a$N(R5)(R6) wherein a=1 or 2 and R5 and R6 are H or lower alkyl, (ix)

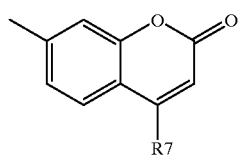

where R7 is H or CF$_3$, (x)

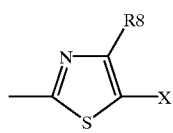

wherein X is H, —NO$_2$, —CO$_2$CH$_3$ or CH$_3$; and R8 is H or CH$_3$, (xi)

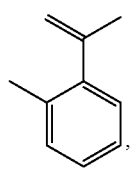

(xii)

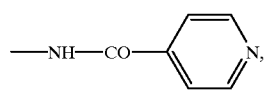

(xiii)

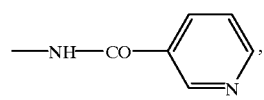

(xiv)

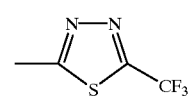

(xv)

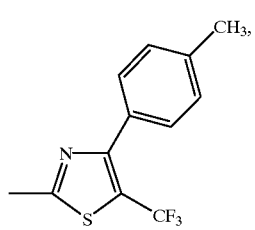

(xvi)

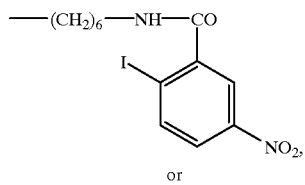

or (xvii)

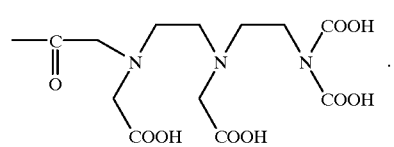

2. A pharmaceutical composition comprising a compound of claim 1 and a pharmaceutically acceptable excipient.

3. A method for treating a neoplastic disease selected from the group consisting of colon adenocarcinoma, myeloma, breast adenocarcinoma, melanoma, lung carcinoma, ovarian adenocarcinoma and leukemia comprising administering to a patient in need thereof, an effective amount of the compound of claim 1.

4. A method for treating a neoplastic disease selected from the group consisting of colon adenocarcinoma, myeloma, breast adenocarcinoma, melanoma, lung carcinoma, ovarian adenocarcinoma and leukemia comprising administering to a patient in need thereof, an effective amount of a compound:

(a)

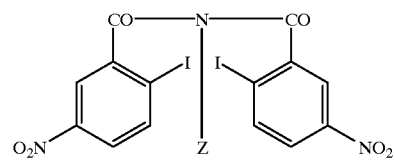

wherein Z is:

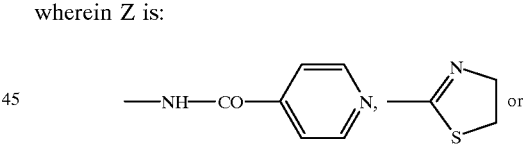

(b)

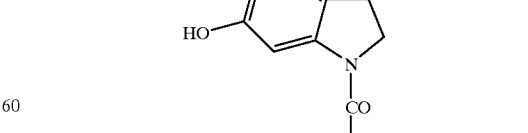

-continued
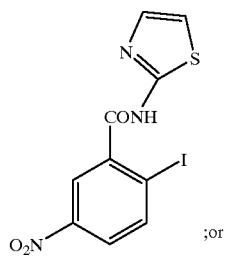
(c)
;or
-continued
(d)
* * * * *